(12) United States Patent
Jess et al.

(10) Patent No.: US 8,334,232 B2
(45) Date of Patent: Dec. 18, 2012

US008334232B2

(54) POROUS HETEROGENEOUS CATALYST COATED WITH AN IONIC LIQUID

(75) Inventors: Andreas Jess, Bayreuth (DE); Wolfgang Korth, Bayreuth (DE); Bastian Etzold, Buchenhof (DE)

(73) Assignee: Sud-Chemie AG (DE)

( * ) Notice: Subject to any disclaimer, the term of this patent is extended or adjusted under 35 U.S.C. 154(b) by 743 days.

(21) Appl. No.: 12/298,246

(22) PCT Filed: Apr. 24, 2007

(86) PCT No.: PCT/EP2007/003595
§ 371 (c)(1),
(2), (4) Date: Feb. 24, 2009

(87) PCT Pub. No.: WO2007/124896
PCT Pub. Date: Nov. 8, 2007

(65) Prior Publication Data
US 2009/0264691 A1 Oct. 22, 2009

(30) Foreign Application Priority Data
Apr. 26, 2006 (DE) .......................... 10 2006 019 460

(51) Int. Cl.
*B01J 31/02* (2006.01)
(52) U.S. Cl. ........ 502/164; 502/150; 502/162; 502/169; 502/173; 502/300; 502/325
(58) Field of Classification Search .................. 585/100, 585/150, 162, 164, 173, 300, 325, 339; 502/100, 502/150, 162, 164, 173, 300, 325, 339, 200
See application file for complete search history.

(56) References Cited

U.S. PATENT DOCUMENTS

| | | | | |
|---|---|---|---|---|
| 4,837,189 A * | 6/1989 | Simon et al. ................ | 502/150 |
| 5,089,245 A | 2/1992 | Eyman et al. | |
| 5,693,585 A | 12/1997 | Benazzi et al. | |
| 6,040,263 A * | 3/2000 | Mussmann et al. ........... | 502/164 |
| 6,969,693 B2 * | 11/2005 | Sauvage et al. ............... | 502/159 |
| 7,381,845 B2 * | 6/2008 | Weiskopf et al. ............. | 564/490 |
| 2002/0198100 A1 * | 12/2002 | Mehnert et al. ............... | 502/150 |

FOREIGN PATENT DOCUMENTS

| | | |
|---|---|---|
| EP | 1 120 159 A1 | 1/2001 |
| WO | WO99/03163 | 1/1999 |
| WO | WO 02094740 A2 * | 11/2002 |
| WO | WO 2005/016855 | 2/2005 |
| WO | WO 2005/123253 | 12/2005 |

OTHER PUBLICATIONS

Zeolyst product list as of Mar. 24, 2005, available through Internet Archive.org.*
Huang, et al., "Pd Nanoparticles Immobilized on Molecular Sieves by Ionic Liquids: Heterogeneous Catalysts for Solvent-Free Hydrogenation" in Angew. Chem. Int. Ed., 2004, 43, 1397-1399.*
Mehnert, et al., "Supported Ionic Liquid Catalysis—A New Concept for Homogeneous Hydroformylation Catalysis" in J. Am. Chem. Soc., 2002, 124, 12932-12933.*
Gallezot, "Hydrogenation—Heterogeneous" in Encyclopedia of Catalysis, John Wiley & Sons, 2002, available on-line Jul. 15, 2002.*
Leofanti, et al., "Surface Area and Pore Texture of Catalysts" in Catalysis Today, 41 (1998), 207-209—month unknown.*
Mikkola, Jyri-Pekka et al., Supported Ionic Liquids Catalysts for Fine Chemicals: Citral Hydrogenation; The Royal Society of Chemistry 2006; Oct. 12, 2005; pp. 197-205; Green Chemistry, vol. 8.
Decastro, C., et al., Immobilised Ionic Liquids as Lewis Acid Catalysts for the Alkylation of Aromatic Compounds with Dodecene; Journal of Catalysis, Academic Press, Duluth, MN, US; Nov. 15, 2000; pp. 86-94; Bd. 96, Nr. 1.
Riisager, Anders et al., Supported Ionic Liquid Phase (SILP) Catalysis: An Innovative Concept for Homogeneous Catalysis in Continuous Fixed-Bed Reactors; European Journal of Inorganic Chemistry 2006; Feb. 2006; pp. 65-706.
Huang, Jun et al., Pd Nanoparticles Immobilized on Molecular Sieves by Ionic Liquids: Heterogeneous Catalysts for Solvent-Free Hydrogenation; Angewandte Chemie 2004, pp. 1421-1423; Nr. 116, Wiley VCH Verlag GmbH & Co. KGaA, Weinheim; 2004.
Mehnert, Christian, Supported Ionic Liquid Catalysis; Chemistry European Journal 2005; pp. 50-56; Nr. 11; Wiley VCH Verlag GmbH & Co. KGaA, Weinheim.
Breitenlechner, Stefan, Solid Catalysts on the Basis of Supported Ionic Liquids and Their Use in Hydroamination reactions; Journal of Molecular Catalysis A: Chemical 214 (2004), Elsevier B.V.; Dec. 2004; pp. 1381-1169; Germany.
International Search Report, dated Jul. 25, 2007.

* cited by examiner

*Primary Examiner* — In Suk Bullock
*Assistant Examiner* — Bradley Etherton
(74) *Attorney, Agent, or Firm* — Schwegman, Lundberg & Woessner, P.A.

(57) ABSTRACT

The invention relates to a porous heterogeneous catalyst. In order to prepare a catalyst which catalyzes with a relatively high selectivity the hydrogenation of individual unsaturated bonds of polyunsaturated compounds it is proposed that the inner surface of the catalysts is coated with an ionic liquid.

9 Claims, 7 Drawing Sheets

POROUS HETEROGENEOUS CATALYST COATED WITH AN IONIC LIQUID

Field of the Invention

The present invention relates to a porous heterogeneous catalyst.

Selective hydrogenation reactions are of great importance for example in the processing of carbon cuts obtained by petroleum treatment to form synthetically valuable intermediate products, such as for example in the selective hydrogenation of aromatic compounds to form cycloolefins, in the hydrogenation of acetylene to form ethylene, in the hydrogenation of butadiene to form 1-butene and/or 2-butene and in the hydrogenation of phenylacetylene to form styrene.

The catalysts used in selective hydrogenation reactions are often supported metal catalysts, for example supported nickel, palladium or platinum catalysts. These catalysts accelerate the desired hydrogenation reaction, but although they also have a certain selectivity in respect of same, the proportion of unwanted by-products is still as a rule relatively high in particular at high conversion rates.

The object of the present invention is therefore to provide a catalyst which catalyzes with a relatively high selectivity the hydrogenation of individual unsaturated bonds of polyunsaturated compounds.

Background of the Invention

This object is achieved starting from a catalyst of the type according to the preamble in that the inner surface of the catalysts is coated with an ionic liquid (IL).

In the hydrogenation of individual unsaturated bonds of polyunsaturated compounds, the catalyst according to the invention has a relatively high selectivity at a relatively high conversion rate.

The catalyst according to the invention can be prepared easily in terms of process engineering and thus cheaply using readily accessible substances. The catalyst according to the invention also has the advantage that it can be used to catalyze reactions in gas or liquid phase. However, to ensure the high selectivity of the catalyst according to the invention for as long as possible, the catalyst is preferably to be subjected only to reaction conditions which essentially do not effect a peeling-off of the IL-coating.

As already stated above, the catalyst according to the invention is a porous heterogeneous catalyst the inner surface of which is coated with an ionic liquid. The porous heterogeneous catalyst itself is a preformed catalyst, i.e. the catalyst according to the invention is prepared by using a fully developed porous heterogeneous catalyst and coating it with the ionic liquid.

The present invention is not limited to specific heterogeneous catalysts which are coated with an ionic liquid. Rather, all heterogeneous catalysts can be coated with an ionic liquid, i.e. including those which are used in selective reactions other than selective hydrogenation. Suitable catalysts contain for example metals which are selected from the group consisting of nickel, cobalt, copper, iron, ruthenium, rhodium, iridium, palladium and platinum. The previously named metal catalysts can optionally also be in the form of skeleton catalysts. The heterogeneous catalysts can be doped or undoped. Suitable doping metals can be selected for example from the elements of groups 3 to 12 of the periodic table of the elements according to IUPAC nomenclature (Handbook of Chemistry and Physics, 80$^{th}$ edition, 1999-2000).

If the catalyst according to the invention comprises a supported metal catalyst, the catalytically active metal is present in a quantity of preferably 0.1 to 60 wt.-%, particularly preferably 1 to 50 wt.-%, in particular 2 to 10 wt.-% relative to the overall weight of the catalyst according to the invention.

As defined by Wasserscheid and Keim in "Angewandte Chemie" 2000, 112, pages 3926-3945, ionic liquids are salts which melt at a relatively low temperature. Ionic liquids are therefore already liquid at relatively low temperatures. In addition, they are in general not combustible and have no measurable vapour pressure.

Within the framework of the present invention, by ionic liquid is meant salts which have a melting point or melting range which is below 200° C., preferably below 150° C. and particularly preferably below 100° C.

Furthermore, preferred ionic liquids are those which have a molar mass of preferably at most 1,000 g/mol, particularly preferably at most 500 g/mol.

Furthermore, preferred ionic liquids are those the cations of which are organic in nature and the anions of which are organic or inorganic in nature.

Ionic liquids are formed from positive and negative ions, but are overall neutral in charge. The positive and also the negative ions are predominantly monovalent, but multivalent anions and/or cations which have up to five, preferably up to four, particularly preferably up to three and particularly preferably up to two electric charges are also possible. The charges within the respective ions are either localized or delocalized.

The present invention is not limited to catalysts the inner surface of which is coated with a specific ionic liquid; all suitable ionic liquids can be used, which also includes mixtures of different ionic liquids.

Depending on the purpose for which the catalyst according to the invention is intended, it can be preferred if the catalyst is a solid catalyst or a supported heterogeneous catalyst.

According to a preferred embodiment of the invention, the catalyst according to the invention is formed as powder or as a shaped body.

The catalyst according to the invention can be used as powder with high yields and selectivities in suspension processes. Typical particle sizes of such powders are 10 to 250 micrometers, but particles much smaller than 1 micrometer can also be used, say when using carbon black as catalyst support.

Shaped bodies are preferably used for example in processes operated in fixed beds. Preferred shaped bodies are spheres, cones, strands, hollow strands, star-shaped strands, solid cylinders, hollow cylinders, tablets, trilobes, grit, etc with characteristic diameters from 0.5 to 5 mm or also monoliths and similarly structured packs (cf. Ullmann's Encyclopedia, Sixth Edition, 2000 Electronic Release, Chapter Fixed-Bed Reactors, Par. 2: Catalyst Forms for Fixed-Bed Reactors).

It was found that by coating a heterogeneous porous catalyst with an ionic liquid the activity of the catalyst can be reduced so markedly that even shaped bodies with a diameter of up to 2 cm can be used without significant losses in respect of product selectivity having to be accepted. Preferred shaped bodies therefore have a diameter or dimensions from 1 mm to 2 cm, preferably from 2 mm to 1.8 cm, preferably from 4 mm to 1.5 cm and more preferably from 6 mm to 1.2 cm.

It can furthermore be preferred that the porous heterogeneous catalyst is a metal catalyst, preferably a solid metal catalyst or a supported metal catalyst. The supported metal catalyst is preferably a supported transition metal catalyst, in particular a supported precious metal catalyst.

It can be preferred that the BET surface area of the catalyst without the IL-coating is 10 to 300 m²/g, preferably 15 to 80 m²/g, particularly preferably 20 to 50 m²/g. The BET surface area is determined by the single-point method by adsorption of nitrogen according to DIN 66132.

It can further be preferred that the BET surface area of the catalyst with the IL-coating is 8 to 240 m²/g, preferably 12 to 64 m²/g, particularly preferably 16 to 40 m²/g.

In addition it can be preferred that the integral pore volume of the catalyst (determined according to DIN 66133 (Hg porosimetry)) without the IL-coating is greater than 100 mm³/g, preferably greater than 180 mm³/g.

It can also be preferred that the integral pore volume of the catalyst with the IL-coating is greater than 80 mm³/g, preferably greater than 144 mm³/g.

According to a preferred embodiment of the catalyst according to the invention, a maximum of 10% of the pore volume of the catalyst without the IL-coating is formed of pores with a radius smaller than 10 nm, preferably a maximum of 8%, preferably a maximum of 6% and particularly preferably a maximum of 5%.

According to a further preferred embodiment of the catalyst according to the invention, a maximum of 10% of the pore volume of the catalyst without the IL-coating is formed of pores with a radius greater than 500 nm, preferably a maximum of 8%, preferably a maximum of 6% and particularly preferably a maximum of 5%.

In a further preferred embodiment of the catalyst according to the invention, it is provided that the average pore diameter of the catalyst without the IL-coating is 10 to 100 nm.

In addition, according to a preferred development of the catalyst according to the invention, the average pore diameter of the catalyst with the IL-coating can be 5 to 100 nm.

Figure 7:
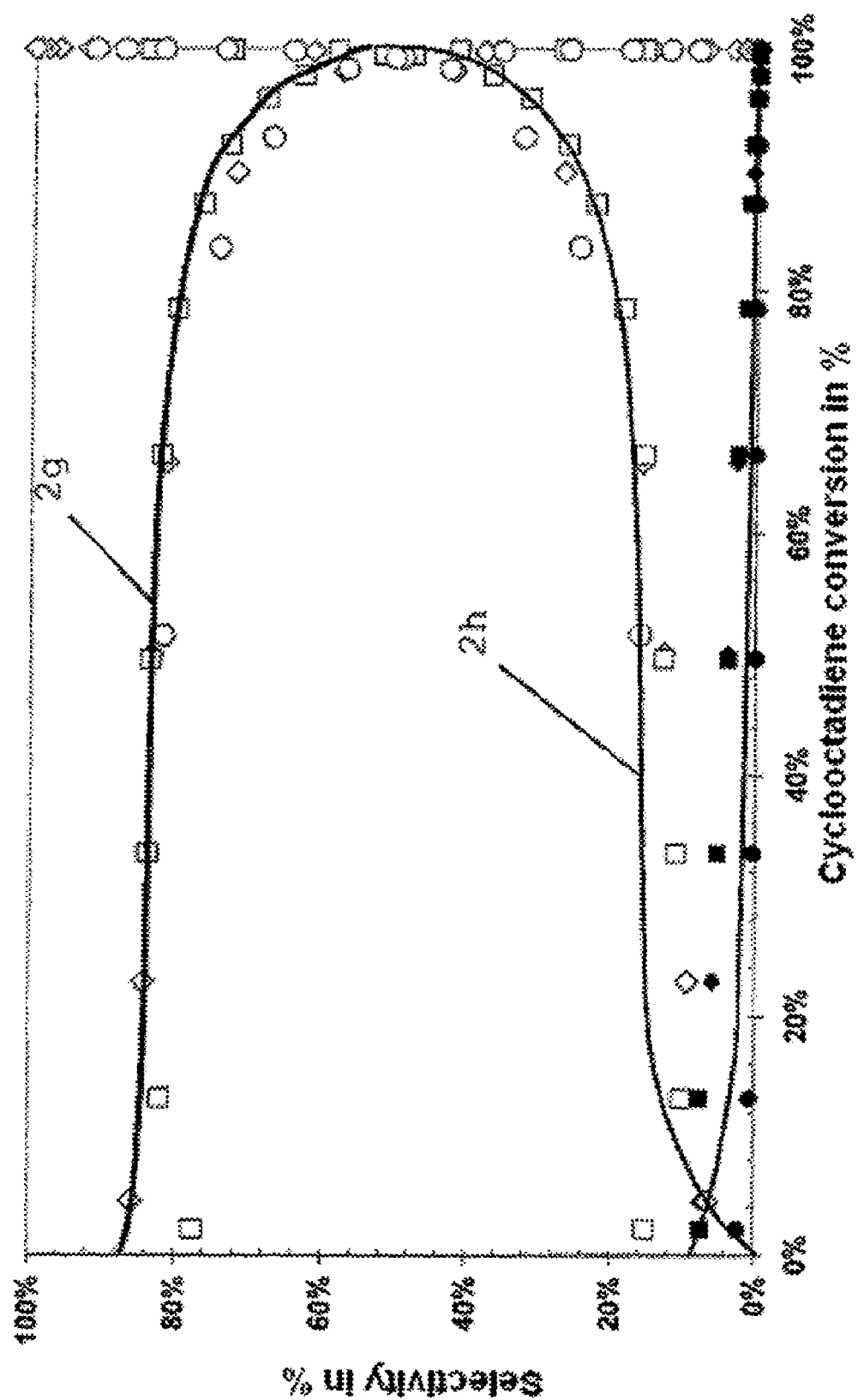

yield in relation to the modified experiment time during the hydrogenation of cyclooctadiene by means of the supported nickel catalyst coated with an ionic liquid;

FIG. 7: selectivity with regard to cis-cyclooctene (curve 2g) and cyclooctane (curve 2h) in relation to the cyclooctadiene conversion during the hydrogenation of cylcooctadiene by means of the supported nickel catalyst coated with an ionic liquid.

DETAILED DESCRIPTION OF THE INVENTION

In principle, within the framework of the present invention the catalyst according to the invention can be coated with any ionic liquid and the cation accordingly be of any type. Preferred as cation are in general for example ammonium or phosphonium ions or cations which contain at least one five- or six-membered heterocycle which has at least one phosphorus or one nitrogen atom and also optionally one oxygen or sulphur atom. Particularly preferred are cations which contain at least one five- or six-membered heterocycle which has one, two or three nitrogen atoms and one sulphur or one oxygen atom. Quite particularly preferred are cations which contain at least one five- or six-membered heterocycle which has one or two nitrogen atoms.

It can be preferred that the cation of the ionic liquid is selected from compounds of general Formulae IL-1 to IL-23 below:

(IL-1)

(IL-2)

(IL-3)

(IL-4)

(IL-5)

(IL-6)

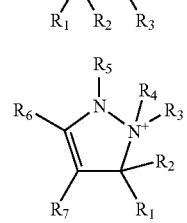

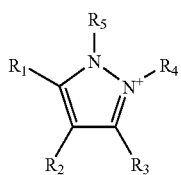
(IL-7)

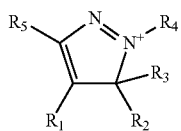
(IL-8)

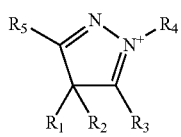
(IL-9)

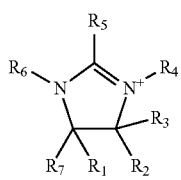
(IL-10)

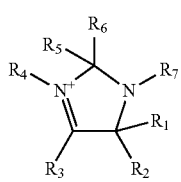
(IL-11)

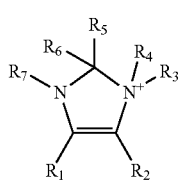
(IL-12)

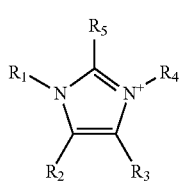
(IL-13)

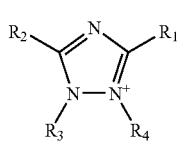
(IL-14)

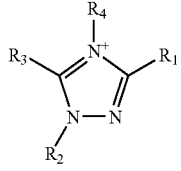
(IL-15)

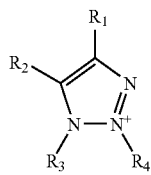
(IL-16)

(IL-17)

(IL-18)

(IL-19)

(IL-20)

(IL-21)

(IL-22)

(IL-23)

in which the radicals $R_1$, $R_2$, $R_3$, $R_4$, $R_5$, $R_6$, $R_7$, $R_8$, $R_9$ and $R_{10}$ each independently of one another can be radicals selected from the group consisting of hydrogen, functional groups, aryl, alkyl, aryloxy, alkyloxy, halogen, heteroatom and/or heterocycle-substituted $C_1$-$C_{18}$ alkyl, $C_2$-$C_{18}$ alkyl; $C_6$-$C_{12}$ aryl, $C_5$-$C_{12}$ cycloalkyl interrupted by one or more non-adjacent oxygen atoms and/or sulphur atoms and/or one or more substituted or unsubstituted imino groups, a five- to six-membered heterocycle having oxygen, nitrogen and/or sulphur atoms,
wherein two of the named radicals can be linked together with formation of an unsaturated or saturated ring segment which can optionally be interrupted by one or more oxygen and/or sulphur atoms and/or one or more substituted or unsubstituted imino groups, wherein the ring segment can be substituted by functional groups, aryl, alkyl, aryloxy, alkyloxy, halogen, heteroatom and/or heterocycle radicals,
and wherein $R_4$ in addition can be selected from the group of radicals consisting of $C_1$-$C_{18}$ alkyloyl, $C_1$-$C_{18}$ alkyloxycarbonyl, $C_5$-$C_{12}$ cycloalkylcarbonyl and $C_6$-$C_{12}$ aryloyl, wherein the members of the named group can each be substituted by one or more functional groups, aryl, alkyl, aryloxy, alkyloxy, halogen, heteroatoms and/or heterocycle radicals, wherein $C_1$-$C_8$, $C_5$-$C_{12}$, or $C_6$-$C_{12}$ refer to the alkyl chain.

There the term functional groups means the group of the following functional groups: aryl-, alkyl-, aryloxy-, alkyloxy-, halogen-, heteroatom- and/or heterocycle-substituted $C_1$-$C_{18}$ alkyl, for example methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, heptadecyl, octadecyl, 1,1-dimethylpropyl, 1,1-dimethylbutyl, 1,1,3,3-tetramethylbutyl, benzyl, 1-phenylethyl, 2-phenylethyl, alpha-alpha-dimethylbenzyl, benzhydryl, p-tolylmethyl, 1-(p-butyl-phenyl)-ethyl, p-chlorobenzyl, 2,4-dichlorobenzyl, p-methoxybenzyl, m-ethoxybenzyl, 2-cyanoethyl, 2-cyanopropyl, 2-methoxycarbonethyl, 2-ethoxycarbonylethyl, 2-butoxycarbonylpropyl, 1,2-di(methoxycarbonyl)-ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chlorethyl, trichloromethyl, trifluoromethyl, 1,1-dimethyl-2-chlorethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, $C_2$-$C_{18}$ alkyl interrupted by one or more non-adjacent oxygen and/or sulphur atoms and/or one or more substituted or unsubstituted imino groups, for example 5-hydroxy-3-oxa-pentyl, 8-hydroxy-3,6-dioxa-octyl, 11-hydroxy-3,6,9-trioxaundecyl, 7-hydroxy-4-oxa-heptyl, 11-hydroxy-4,8-dioxaundecyl, 15-hydroxy-4,8,12-trioxa-pentadecyl, 9-hydroxy-5-oxanonyl, 14-hydroxy-5,10-oxatetradecyl, 5-methoxy-3-oxapentyl, 8-methoxy-3,6-dioxaoctyl, H-methoxy-3,6,9-trioxaundecyl, 7-methoxy-4-oxa-heptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxa-nonyl and 14-ethoxy-5,10-oxatetradecyl.

If two radicals form a ring with each other, these radicals can preferably together stand for 1,3-propylene, 1,4-butylene, 2-oxa-1,3-propylene, 1-oxa-1,3-propylene, 2-oxa-1,3-propylene, 1-oxa-1,3-propenylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene.

The number of oxygen and/or sulphur atoms and/or imino groups in the preferred cations of the ionic liquid is not limited. In general, it is no more than 5 per radical, preferably no more than 4, in particular no more than 3. Furthermore, there is at least one carbon atom, particularly preferably at least two, between two heteroatoms.

Preferred imino groups can be for example imino, methylimino, iso-propylimino, n-butylimino or tert-butylimino.

Furthermore, the term functional groups stands for the group of functional groups below: carboxy, carboxamide, hydroxy, di-($C_1$-$C_4$-alkyl)amino, $C_1$-$C_4$ alkyloxycarbonyl, cyano, $C_1$-$C_4$ alkyloxy, $C_6$-$C_{12}$ aryl substituted by functional groups, aryl, alkyl, aryloxy, alkyloxy, halogen, heteroatoms and/or heterocycles, for example phenyl, tolyl, xylyl, alpha-naphthyl, beta-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-diethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxyethylphenyl, $C_5$-$C_{12}$ cycloalkyl substituted by functional groups, aryl, alkyl, aryloxy, alkyloxy, halogen, heteroatoms and/or heterocycles, for example cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl or dichlorocyclopentyl, saturated or unsaturated bicyclic systems, e.g. norbornyl or norbornenyl, a five- to six-membered heterocycle having oxygen, nitrogen and/or sulphur atoms, for example furyl, thiophenyl, pyrryl, pyridyl, indolyl, benzoxazolyl, dioxolyl, dioxyl, benzimidazolyl, benzthiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl, and a $C_1$-$C_4$ alkyl, for example methyl, ethyl, propyl, isopropyl, n-butyl, sec-butyl or tert-butyl.

$C_1$-$C_{18}$ alkyloyl(alkylcarbonyl) can for example be acetyl, propionyl, n-butyloyl, sec-butyloyl, tert-butyloyl, 2-ethylhexylcarbonyl, decanoyl, dodecanoyl, chloroacetyl, trichloroacetyl or trifluoroacetyl.

$C_1$-$C_{18}$ alkyloxycarbonyl can for example be methyloxycarbonyl, ethyloxycarbonyl, propyloxycarbonyl, isopropyloxycarbonyl, n-butyloxycarbonyl, sec-butyloxycarbonyl, tert-butyloxycarbonyl, hexyloxycarbonyl, 2-ethylhexyloxycarbonyl or benzyloxycarbonyl.

$C_5$-$C_{12}$ cycloalkylcarbonyl can for example be cyclopentylcarbonyl, cyclohexylcarbonyl or cyclododecylcarbonyl.

$C_5$-$C_{12}$ aryloyl(arylcarbonyl) can for example be benzoyl, toluoyl, xyloyl, alpha-naphthoyl, beta-naphthoyl, chlorobenzoyl, dichlorobenzoyl, trichlorobenzoyl or trimethylbenzoyl.

Preferred are $R_1$, $R_2$, $R_3$, $R_5$, $R_6$, $R_7$, $R_8$, $R_9$ and $R_{10}$ each independently of one another, hydrogen, methyl, ethyl, n-butyl, 2-hydroxyethyl, 2-cyanoethyl, 2-(methoxycarbonyl)-ethyl, 2-ethoxycarbonyl-ethyl, 2-n-butoxycarbonyl-ethyl, dimethylamino, diethylamino or chlorine.

$R_4$ is preferably methyl, ethyl, n-butyl, 2-hydroxyethyl, 2-cyanoethyl, 2-methoxycarbonyl-ethyl, 2-ethoxycarbonyl-ethyl, 2-n-butoxycarbonyl-ethyl, acetyl, propionyl, t-butyryl, methoxycarbonyl, ethoxycarbonyl or n-butoxycarbonyl.

Particularly preferred ammonium ions (IL-1) are those in which, independently of one another, $R_4$ is selected from acetyl, methyl, ethyl or n-butyl and $R_1$, $R_2$ and $R_3$ are selected from methyl, ethyl, n-butyl, 2-hydroxyethyl, benzyl or phenyl.

Particularly preferred phosphonium ions (IL-1) are those in which, independently of one another, $R_4$ is selected from acetyl, methyl, ethyl or n-butyl and $R_1$, $R_2$ and $R_3$ are selected from phenyl, phenoxy, ethoxy and n-butoxy.

Particularly preferred pyrrolidinium ions (IL-3) are those in which, independently of one another, $R_3$ and $R_4$ are selected from acetyl, methyl, ethyl or n-butyl and all other radicals stand for hydrogen.

Particularly preferred 1-pyrazolinium ions (IL-4) are those in which, independently of one another, all radicals up to $R_4$ are selected from hydrogen or methyl and $R_4$ is selected from acetyl, methyl, ethyl or n-butyl.

Particularly preferred 2-pyrazolinium ions (IL-5) are those in which, independently of one another, $R_5$ is selected from hydrogen, methyl, ethyl or phenyl, $R_4$ from acetyl, methyl, ethyl or n-butyl and the other radicals from hydrogen or methyl.

Particularly preferred 3-pyrazolinium ions (IL-6) are those in which, independently of one another, $R_3$ and $R_5$ are selected from hydrogen, methyl, ethyl or phenyl, $R_4$ from acetyl, methyl, ethyl or n-butyl and the remaining radicals from hydrogen or methyl.

Particularly preferred 1H-pyrazolinium ions (IL-7) are those in which, independently of one another, $R_5$ is selected from hydrogen, methyl or ethyl, $R_1$, $R_2$ and $R_3$ from hydrogen or methyl and $R_4$ from acetyl, methyl, ethyl or n-butyl.

Particularly preferred 3H-pyrazolinium ions (IL-8) are those in which, independently of one another, $R_2$ is selected from hydrogen, methyl or ethyl, $R_1$, $R_3$ and $R_5$ from hydrogen or methyl and $R_4$ from acetyl, methyl, ethyl or n-butyl.

Particularly preferred 4H-pyrazolinium ions (IL-9) are those in which, independently of one another, $R_1$, $R_2$, $R_3$ and $R_5$ are selected from hydrogen or methyl and $R_4$ from acetyl, methyl, ethyl or n-butyl.

Particularly preferred imidazolinium ions (IL-10) are those in which, independently of one another, $R_5$ or $R_6$ is selected from hydrogen, methyl or ethyl, $R_4$ from acetyl, methyl, ethyl or n-butyl and the other radicals from hydrogen or methyl.

Particularly preferred imidazolinium ions (IL-11) are those in which, independently of one another, $R_5$, $R_6$ or $R_7$ is selected from hydrogen, methyl or ethyl, $R_4$ from acetyl, methyl, ethyl or n-butyl and the other radicals from hydrogen or methyl.

Particularly preferred imidazolinium ions (IL-12) are those in which, independently of one another, $R_3$ or $R_7$ is selected from hydrogen, methyl, ethyl, n-butyl or phenyl, $R_4$ from acetyl, methyl, ethyl or n-butyl and $R_5$ or $R_6$ from hydrogen, methyl or ethyl and $R_1$ or $R_2$ from hydrogen or methyl.

Particularly preferred imidazolium ions (IL-13) are those in which, independently of one another, $R_1$ is selected from the group consisting of methyl, ethyl, n-propyl, n-butyl, n-pentyl, n-octyl, n-decyl, n-dodecyl, 2-hydroxyethyl and 2-cyanoethyl, $R_4$ from acetyl, methyl, ethyl or n-butyl and the other radicals independently from one another from hydrogen, methyl or ethyl.

Particularly preferred 1,2,4-triazolium ions (IL-14) and (IL-15) are those in which, independently of one another, $R_1$ or $R_2$ and $R_1$ or $R_3$ respectively are selected from hydrogen, methyl, ethyl, or phenyl, $R_4$ from acetyl, methyl, ethyl or n-butyl and $R_3$ or $R_2$ from hydrogen, methyl or phenyl. Particularly preferred 1,2,3-triazolium ions (IL-16) and (IL-17) are those in which, independently of one another, $R_3$ and $R_1$ respectively are selected from hydrogen, methyl or ethyl, $R_4$ from acetyl, methyl, ethyl or n-butyl and $R_1$ or $R_2$ and $R_2$ or $R_3$ respectively from hydrogen or methyl or $R_1$ and $R_2$ and $R_2$ and $R_3$ respectively, 1,4-buta-1,3-dienylene and all other radicals are hydrogen.

Particularly preferred thiazolium ions (IL-18) or oxazolium ions (IL-19) are those in which, independently of one another, $R_1$ is selected from hydrogen, methyl, ethyl, or phenyl, $R_4$ from acetyl, methyl, ethyl or n-butyl and $R_2$ or $R_3$ from hydrogen or methyl.

Particularly preferred pyridinium ions (IL-20) are those in which one of the radicals $R_1$, $R_2$, $R_3$, $R_5$ and $R_6$ is methyl, ethyl or chlorine, $R_4$ is acetyl, methyl, ethyl or n-butyl and all other radicals are hydrogen, or $R_1$ is dimethylamino, $R_4$ acetyl, methyl, ethyl or n-butyl and all other radicals are hydrogen or $R_4$ is acetyl, methyl, ethyl or n-butyl and all other radicals are hydrogen or $R_2$ is carboxy or carboxamide, $R_4$ is acetyl, methyl, ethyl or n-butyl and all other radicals are hydrogen or $R_2$ and $R_3$ or $R_2$ and $R_1$ are 1,4-buta-1,3-dienylene, $R_4$ is acetyl, methyl, ethyl or n-butyl and all other radicals are hydrogen.

Particularly preferred pyrimidinium ions (IL-21) are those in which $R_1$, $R_4$ and $R_5$ are hydrogen or methyl, $R_4$ is acetyl, methyl, ethyl or n-butyl and $R_3$ is hydrogen, methyl or ethyl, or $R_2$ and $R_5$ are methyl, $R_1$ is hydrogen and $R_3$ is hydrogen, methyl or ethyl and $R_4$ is acetyl, methyl, ethyl or n-butyl.

Particularly preferred pyridazinium ions (IL-22) are those in which one of the radicals $R_1$, $R_2$, $R_3$ and $R_5$ is methyl or ethyl, $R_4$ is acetyl, methyl, ethyl or n-butyl and all other radicals are hydrogen or $R_4$ is acetyl, methyl, ethyl or n-butyl, and all other radicals are hydrogen.

Particularly preferred pyrazinium ions (IL-23) are those in which $R_1$, $R_2$, $R_3$ and $R_5$ are all methyl and $R_4$ is acetyl, methyl, ethyl or n-butyl or $R_4$ is acetyl, methyl, ethyl or n-butyl, and all other radicals are hydrogen.

Of the abovenamed cation groups IL-1 to IL-23, the named ammonium, phosphonium, pyridinium and imidazolium ions are particularly preferred.

Quite particularly preferred as cations are 1,2-dimethylpyridinium, 1-methyl-2-ethylpyridinium, 1-methyl-2-ethyl-6-methylpyridinium, N-methylpyridinium, 1-butyl-2-methylpyridinium, 1-butyl-2-ethylpyridinium, 1-butyl-2-ethyl-6-methylpyridinium, N-butylpyridinium, 1-butyl-4-methylpyridinium, 1,3-dimethylimidazolium, 1,2,3-trimethylimidazolium, 1-n-butyl-3-methylimidazolium, 1,3,4,5-tetramethylimidazolium, 1,3,4-trimethylimidazolium, 2,3-dimethylimidazolium, 1-butyl-2,3-dimethylimidazolium, 3,4-dimethylimidazolium, 2-ethyl-3,4-dimethylimidazolium, 3-methyl-2-ethylimidazole, 3-butyl-1-methylimidazolium, 3-butyl-1-ethylimidazolium, 3-butyl-1,2-dimeraylimidazolium, 1,3-di-n-butylimidazolium, 3-butyl-1,4,5-trimethylimidazolium, 3-butyl-1,4-dimethylimidazolium, 3-butyl-2-methylimidazolium, 1,3-dibutyl-2-methylimidazolium, 3-butyl-4-methylimidazolium, 3-butyl-2-ethyl-4-methylimidazolium and 3-butyl-2-ethylimidazolium, 1-methyl-3-octylimidazolium, 1-decyl-3-methylimidazolium.

Particularly preferred are 1-butyl-4-methylpyridinium, 1-n-butyl-3-methylimidazolium and 1-n-butyl-3-ethylimidazolium.

Cations which are derived from diazabicyclononene or diazabicycloundecene are also possible.

Analogously to the above statements the anion of the ionic liquid can be of any type. It is, however, preferred if the anion of the ionic liquid is selected from the group consisting of $F^-$, $Cl^-$, $Br^-$, $I^-$, $PF_6^-$, $BF_4^-$, alkyl sulphate, preferably a $C_1$ to $C_{18}$ alkyl sulphate, ether sulphate, acetate, trifluoroacetate, triflate, sulphate, hydrogensulphite, methyl sulphate, ethyl sulphate, sulphite, hydrogensulphite, aluminium chlorides, preferably $AlCl_4^-$, $Al_2Cl_7^-$ or $Al_3Cl_{10}^-$, aluminium tribromide, nitrite, nitrate, metal complexes, for example metal halides such as copper chloride $CuCl_2^-$, phosphates, phosphate, hydrogen phosphate, dihydrogen phosphate, carbonate, hydrogen carbonate, sulphonate, tosylate, bis(trifluoromethylsulphonyl)imide, cyanide and isocyanate.

By ether sulphates are meant present compounds of the general Formula

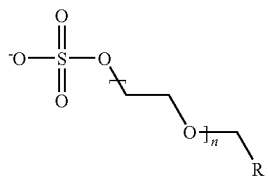

in which n is an integer from 1 to 8 and R is an alkyl radical from $C_1$ to $C_{18}$.

It was found that the advantageous effects of the catalyst according to the invention are particularly clear if the average thickness of the IL-coating is at least equal to the thickness of an individual ion layer of the ionic liquid. According to a preferred embodiment of the catalyst according to the invention the IL-coating has an average thickness which is equal to the thickness of the individual ion layer of the ionic liquid or which is greater than the thickness of an individual ion layer of the ionic liquid, preferably greater than the thickness of 1.1 ion layers, preferably greater than the thickness of 1.2 ion layers, further preferably greater than the thickness of 1.3 ion layers, particularly preferably greater than the thickness of 1.4 ion layers and further particularly preferably greater than the thickness of 1.5 ion layers. By ion layer is meant within the framework of the present invention a single-layer coating of an anion/cation pair of the ionic liquid.

It is further preferred that the IL-coating has an average thickness which is greater than the thickness of 1.6 ion layers of the ionic liquid, preferably greater than the thickness of 1.7 ion layers, preferably greater than the thickness of 1.8 ion layers, further preferably greater than the thickness of 1.9 ion layers, particularly preferably greater than the thickness of at least 2.0 ion layers and further particularly preferably greater than the thickness of at least 2.1 ion layers.

It can further be preferred that the IL-coating has an average thickness which is greater than the thickness of 2.2 ion layers of the ionic liquid, preferably greater than the thickness of 2.3 ion layers, preferably greater than the thickness of 2.4 ion layers, further preferably greater than the thickness of 2.5 ion layers, particularly preferably greater than the thickness of at least 2.6 ion layers and further particularly preferably greater than the thickness of at least 2.7 ion layers.

It can also be preferred that the IL-coating has an average thickness which is greater than the thickness of 2.8 ion layers of the ionic liquid, preferably greater than the thickness of 2.9 ion layers, preferably greater than the thickness of 3.0 ion layers, further preferably greater than the thickness of 3.1 ion layers, particularly preferably greater than the thickness of at least 3.2 ion layers and further particularly preferably greater than the thickness of at least 3.3 ion layers.

It can also be preferred that the IL-coating has an average thickness which is greater than the thickness of 3.4 ion layers of the ionic liquid, preferably greater than the thickness of 3.5 ion layers, preferably greater than the thickness of 3.6 ion layers, further preferably greater than the thickness of 3.7 ion layers, particularly preferably greater than the thickness of at least 3.8 ion layers and further particularly preferably greater than the thickness of at least 3.9 ion layers.

In principle the IL-coating can have a very great thickness. If, however, the layer thickness is further increased beyond a defined layer thickness, this then simply leads to a reduction in the activity of the catalyst while the selectivity remains the same. In another embodiment of the catalyst according to the invention it is preferred that the IL-coating has an average thickness which is less than the thickness of 40 ion layers of the ionic liquid, preferably less than the thickness of 38 ion layers, preferably less than the thickness of 36 ion layers, further preferably less than the thickness of 34 ion layers, particularly preferably less than the thickness of 32 ion layers and further particularly preferably less than the thickness of 30 ion layers.

It can also be preferred that the IL-coating has an average thickness which is less than the thickness of 28 ion layers of the ionic liquid, preferably less than the thickness of 26 ion layers, preferably less than the thickness of 24 ion layers, further preferably less than the thickness of 22 ion layers, particularly preferably less than the thickness of 20 ion layers and further particularly preferably less than the thickness of 19 ion layers.

It can also be preferred that the IL-coating has an average thickness which is less than the thickness of 18 ion layers of the ionic liquid, preferably less than the thickness of 17 ion layers, preferably less than the thickness of 16 ion layers, further preferably less than the thickness of 15 ion layers, particularly preferably less than the thickness of 14 ion layers and further particularly preferably less than the thickness of 13 ion layers.

It can further be preferred that the IL-coating has an average thickness which is less than the thickness of 12 ion layers of the ionic liquid, preferably less than the thickness of 11 ion layers, preferably less than the thickness of 10 ion layers, further preferably less than the thickness of 9.5 ion layers, particularly preferably less than the thickness of 9 ion layers and further particularly preferably less than the thickness of 8.8 ion layers.

It can also be preferred that the IL-coating has an average thickness which is less than the thickness of 8.6 ion layers of the ionic liquid, preferably less than the thickness of 8.4 ion layers, preferably less than the thickness of 8.2 ion layers, further preferably less than the thickness of 8 ion layers, particularly preferably less than the thickness of 7.8 ion layers and further particularly preferably less than the thickness of 7.6 ion layers.

It can also preferably be provided that the IL-coating has an average thickness which is less than the thickness of 7.4 ion layers of the ionic liquid, preferably less than the thickness of 7.2 ion layers, preferably less than the thickness of 7.0 ion layers, further preferably less than the thickness of 6.8 ion layers, particularly preferably less than the thickness of 6.6 ion layers and further particularly preferably less than the thickness of 6.4 ion layers.

It can also be preferred that the IL-coating has an average thickness which is less than the thickness of 6.2 ion layers of the ionic liquid, preferably less than the thickness of 6 ion layers, preferably less than the thickness of 5.8 ion layers, further preferably less than the thickness of 5.6 ion layers, particularly preferably less than the thickness of 5.4 ion layers and further particularly preferably less than the thickness of 5.2 ion layers.

It can also be preferred that the IL-coating has an average thickness which is less than the thickness of 5 ion layers of the ionic liquid, preferably less than the thickness of 4.8 ion layers, preferably less than the thickness of 4.6 ion layers, further preferably less than the thickness of 4.4 ion layers, particularly preferably less than the thickness of 4.2 ion layers and further particularly preferably less than the thickness of 4 ion layers.

According to a further preferred embodiment of the process according to the invention the IL-coating has an average thickness which is greater than the thickness of an ion layer of the ionic liquid and which is less than the thickness of 10 ion layers of the ionic liquid, preferably greater than the thickness of 1.1 ion layers and less than the thickness of 9.8 ion layers, preferably greater than the thickness of 1.2 ion layers and less than the thickness of 9.6 ion layers, further preferably greater than the thickness of 1.3 ion layers and less than the thickness of 9.4 ion layers, more preferably greater than the thickness of 1.4 ion layers and less than the thickness of 9.2 ion layers, even more preferably greater than the thickness of 1.5 ion layers and less than the thickness of 9 ion layers and particularly preferably greater than the thickness of 1.6 ion layers and less than the thickness of 8.8 ion layers.

According to another preferred embodiment of the catalyst according to the invention it is provided that the IL-coating has an average thickness which is greater than the thickness of 1.7 ion layers of the ionic liquid and which is less than the thickness of 8.6 ion layers of the ionic liquid, preferably greater than the thickness of 1.8 ion layers and less than the thickness of 8.4 ion layers, preferably greater than the thickness of 1.9 ion layers and less than the thickness of 8.2 ion layers, more preferably greater than the thickness of 2 ion layers and less than the thickness of 8 ion layers, more preferably greater than the thickness of 2.1 ion layers and less than the thickness of 7.8 ion layers, even more preferably greater than the thickness of 2.2 ion layers and less than the thickness of 7.6 ion layers and particularly preferably greater than the thickness of 2.3 ion layers and less than the thickness of 7.4 ion layers.

In another preferred embodiment of the catalyst according to the invention it is provided that the IL-coating has an average thickness which is greater than the thickness of 2.4 ion layers of the ionic liquid and which is less than the thickness of 7.2 ion layers of the ionic liquid, preferably greater than the thickness of 2.5 ion layers and less than the thickness of 7 ion layers, preferably greater than the thickness of 2.6 ion layers and less than the thickness of 6.8 ion layers, more preferably greater than the thickness of 2.7 ion layers and less than the thickness of 6.6 ion layers, more preferably greater than the thickness of 2.8 ion layers and less than the thickness of 6.4 ion layers, even more preferably greater than the thickness of 2.9 ion layers and less than the thickness of 6.2 ion layers and particularly preferably greater than the thickness of 3 ion layers and less than the thickness of 6 ion layers.

It can also preferably be provided that the IL-coating has an average thickness which is greater than the thickness of 3.1 ion layers of the ionic liquid and which is less than the thickness of 5.8 ion layers of the ionic liquid, preferably greater than the thickness of 3.2 ion layers and less than the thickness of 5.6 ion layers, preferably greater than the thickness of 3.3 ion layers and less than the thickness of 5.4 ion layers, more preferably greater than the thickness of 3.4 ion layers and less than the thickness of 5.2 ion layers, more preferably greater than the thickness of 3.5 ion layers and less than the thickness of 5 ion layers, even more preferably greater than the thickness of 3.6 ion layers and less than the thickness of 4.8 ion layers and particularly preferably greater than the thickness of 3.7 ion layers and less than the thickness of 4.6 ion layers.

It is particularly preferred that the IL-coating has an average thickness which is greater than/equal to the thickness of 1 ion layer(s) of the ionic liquid and which is less than the thickness of 10 ion layers of the ionic liquid, preferably greater than the thickness of 2 ion layers and less than the thickness of 9 ion layers, preferably greater than the thickness of 3 ion layers and less than the thickness of 8 ion layers, more preferably greater than the thickness of 4 ion layers and less than the thickness of 7 ion layers, more preferably greater than the thickness of 5 ion layers and less than the thickness of 6 ion layers.

According to another preferred embodiment of the catalyst according to the invention it is provided that the IL-coating has an average thickness from 0.15 to 10 nm, preferably an average thickness from 0.16 to 9.5 nm, preferably a thickness from 0.17 to 9 nm, further preferably a thickness from 0.18 to 8.5 nm, particularly preferably a thickness from 0.19 to 8 nm and most preferably a thickness from 0.2 to 7.5 nm.

It can be preferred that the IL-coating has an average thickness from 0.21 to 7 nm, preferably an average thickness from 0.22 to 6.5 nm, preferably a thickness from 0.23 to 6 nm, further preferably a thickness from 0.24 to 5.5 nm, particularly preferably a thickness from 0.25 to 5 nm and most preferably a thickness from 0.26 to 4.5 nm.

It can also be preferred that the IL-coating has an average thickness from 0.27 to 4 nm, preferably an average thickness from 0.28 to 3.5 nm, preferably a thickness from 0.29 to 3 nm, further preferably a thickness from 0.3 to 2.5 nm, particularly preferably a thickness from 0.3 to 2 nm and most preferably a thickness from 0.3 to 1.5 nm.

It can also be preferred that the IL-coating an average thickness from 0.3 to 1.3 nm, preferably an average thickness from 0.3 to 1.2 nm, preferably a thickness from 0.3 to 1.1 nm, further preferably a thickness from 0.3 to 1 nm, particularly preferably a thickness from 0.3 to 0.8 nm and most preferably a thickness from 0.3 to 0.6 nm.

According to another preferred embodiment of the catalyst according to the invention it is provided that the IL-coating has an average thickness from 0.17 to 1.7 nm, preferably a thickness from 0.34 to 1.53 nm, preferably a thickness from 0.51 to 1.36 nm, further preferably a thickness from 0.68 to 1.19 nm, and particularly preferably a thickness from 0.85 to 1.02 nm.

According to a further preferred embodiment of the catalyst according to the invention it is provided that a homogeneous catalyst is contained in the IL-coating.

According to a further preferred embodiment of the catalyst according to the invention it is provided that the porous heterogeneous catalyst is a supported catalyst, wherein the catalyst support is prepared using a material selected from the group consisting of titanium oxide, silicon oxide, aluminium oxide, zirconium oxide, magnesium oxide, silicon carbide, magnesium silicate, zinc oxide, zeolites and nanomaterials, such as for example carbon nanotubes or carbon nanofibres.

The above-named oxidic support materials can preferably be used for example in the form of mixed oxides or a defined composition, for example $TiO_2$, $SiO_2$, $Al_2O_3$, $ZrO_2$, $MgO$, $SiC_2$ or $ZnO$. Furthermore preferably carbon blacks, acetylene black, coal, graphite, hydrotalcites or further support materials known per se to a person skilled in the art can be used in different possible modifications. The support materials can preferably be doped with, say, alkaline or alkaline-earth metals or also with phosphorous, halide and/or sulphate salts. Generally, the acid/base properties are modified by such dopings, which can have a positive effect on the catalytic properties. The previously-named hydrogenation-active metals can be deposited on the carrier by any suitable process, for example by impregnation, ion exchange, coprecipitation, e.g. joint precipitation with the carrier, precipitation onto a previously introduced carrier, ion exchange or chemical vapour deposition (CVD).

The invention also relates to a process for the preparation of a porous heterogeneous catalyst, the inner surface of which is coated with an ionic liquid, comprising the following steps:
a) the dissolving of an ionic liquid in a suitable solvent;
b) the bringing of a porous heterogeneous catalyst into contact with the solvent containing the ionic liquid according to step a);
c) the removal of the solvent.

It is preferred that the porous heterogeneous catalyst is a catalyst according to the invention.

The invention also relates to a catalyst which can be obtained by the above process with the steps a) to c).

The invention also relates to a process for the preparation of a porous heterogeneous catalyst, the inner surface of which is coated with an ionic liquid, comprising the following steps:
a) the dissolving of an ionic liquid in a suitable solvent;
b) the introduction of the catalyst into a chamber, in which a flow brought about by the application of suction to the chamber and a below-atmospheric pressure prevails;
c) the introduction into the chamber of the solvent containing the ionic liquid;
d) the formation of a mixture of gas and the solvent containing the ionic liquid;
e) the continuous passing of the mixture from step d) through the catalyst;
f) the removal of the solvent.

The gas used is a protective gas such as for example a noble gas or also nitrogen. The gas is used to prevent a decomposition of the ionic liquid by components of the air.

It is preferred that the below-atmospheric pressure brought about by the suction in the chamber is below 800 mbar.

It is also preferred that the process is carried out at a pressure of 300 mbar to 500 mbar.

It can also be preferred that, during the formation of the mixture of gas and the solvent containing the ionic liquid, drops with an average diameter of 1 micrometer to 900 micrometers are formed.

The invention also relates to a catalyst which can be obtained by the above process with the steps a) to f).

The invention also relates to the use of the catalyst according to the invention for the selective hydrogenation of unsaturated groups of polyunsaturated compounds, in particular for the hydrogenation of aromatic compounds to form cycloolefins, for the hydrogenation of acetylene to form ethylene, for the hydrogenation of diolefins into monoolefins, in particular for the hydrogenation of butadiene to form 1-butene and/or 2-butene, for the hydrogenation of phenylacetylene to form styrene, for the hydrogenation of methylacetylene and propadiene to form propene, for the hydrogenation of olefins and diolefins in aromatic flows without loss of aromatics or for the hydrogenation of cyclododecatriene to form cyclododecene.

EXAMPLE 1

A Süd-Chemie AG G-33 RS supported nickel catalyst, which is commercially available in the form of tablets measuring 6×6 mm, was ground into a powder by means of a ball mill. The particles with a diameter in the range of 125-250 micrometers were separated from the ground product and were exposed to a reductive hydrogen atmosphere, heated to a temperature of 300° C., in order to activate the nickel metal.

The thus-activated, uncoated nickel catalyst (catalyst without IL-coating) was used as a comparison example in the subsequent measurements and reactions.

EXAMPLE 2

To prepare the catalyst according to the invention, 0.8145 g of the uncoated activated nickel catalyst prepared as in Example 1 above was suspended in a solution of 100 ml $CH_2Cl_2$ and 0.05 g 1-butyl-3-methyl-imidazolium octyl sulphate as an ionic liquid under a protective nitrogen atmosphere and the solvent $CH_2Cl_2$ evaporated off under vacuum on the rotary evaporator.

EXAMPLE 3

The pore system of the activated nickel catalyst without IL-coating according to Example 1 and of the nickel catalyst provided with an IL-coating according to Example 2 were characterized by means of BET and Hg porosimetry measurements.

Figure 1:
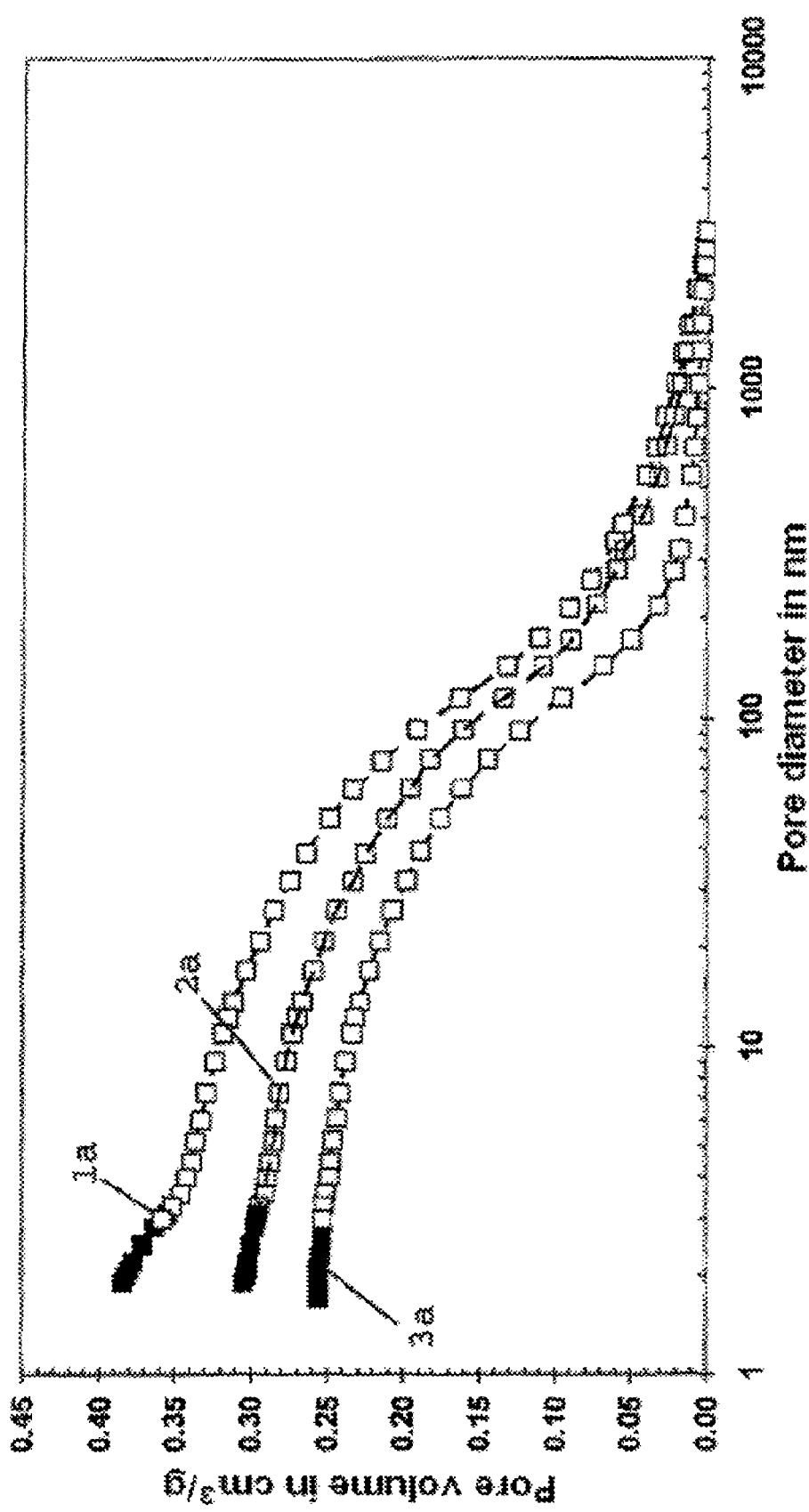
FIG. 1: a graphical representation of the relationship, ascertained by means of BET and Hg porosimetry measurements, between the pore volume and the pore diameter of a supported nickel catalyst without IL-coating (curve 1a), and as comparison example, of a nickel catlyst according to the invention coated with an ionic liquid (curve 2a) and of the catalyst according to the invention (curve 3a), after this has been used in a hydrogenation reaction.

FIG. 1 shows the relationship between the pore volume of the coated and uncoated catalysts and the pore diameter. The curves 1a and 2a of the uncoated and coated catalyst respectively show that the pores of the coated catalyst are coated with the ionic liquid in a substantially uniform thickness, largely regardless of their diameter. The data showed that the IL-coating covers approx. 22 vol.-% of the original volume of the uncoated nickel catalyst.

Figure 2:
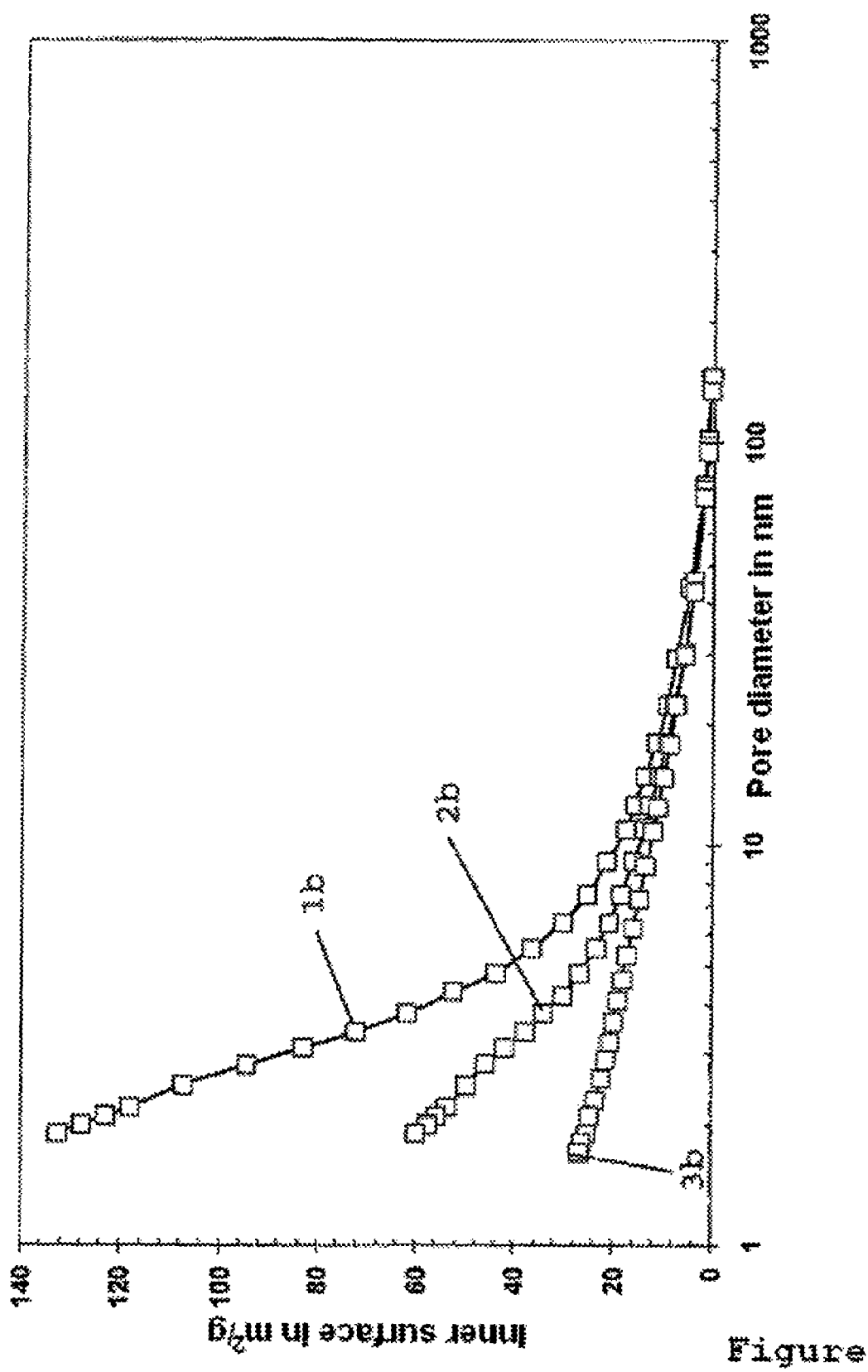
FIG. 2: a graphical representation of the relationship, ascertained by means of BET and Hg porosimetry measurements, between the inner surface and the pore diameter of the supported nickel catalyst without IL-coating (curve 1b), the nickel catalyst according to the invention coated with an ionic liquid (curve 2b), and the catalyst according to the invention (curve 3b) after this has been used in a hydrogenation reaction.

FIG. 2 shows the relationship between the inner surface of the uncoated and coated nickel catalyst and the pore diameter. The curves 1b and 2b of the uncoated and coated nickel catalysts respectively show that, due to the IL-coating, the inner surface of the coated catalyst is reduced by approximately 45% compared with the uncoated catalyst. An average thickness of the IL-coating of approx. 0.6 nm can be calculated from this.

EXAMPLE 4

In order to ascertain a measure of the activity of the uncoated nickel catalyst and that coated with the ionic liquid, the two named catalysts were used in the reaction of cyclooctadiene with hydrogen.

The hydrogenation of cyclooctadiene by means of the uncoated nickel catalyst took place within the following reaction parameters:
$d_{cat}$=125-250 micrometers
$M^0_{cyclooctadiene}$=0.178 g
$V_{dodecane}$=150 ml
T=50° C.
$p_{H2}$=50 bar
n=2000 l/min
$m_{cat}$=0.1134.

The hydrogenation of cyclooctadiene by means of the nickel catalyst coated with the ionic liquid took place under the following reaction conditions:
$d_{cat}$=125-250 micrometers
$m^0_{cyclooctadiene}$=0.172 g
$V_{dodecane}$=150 ml
T=50° C.
$p_{H2}$=50 bar
n=2000 l/min
$m_{cat}$=0.8145.

Figure 3:
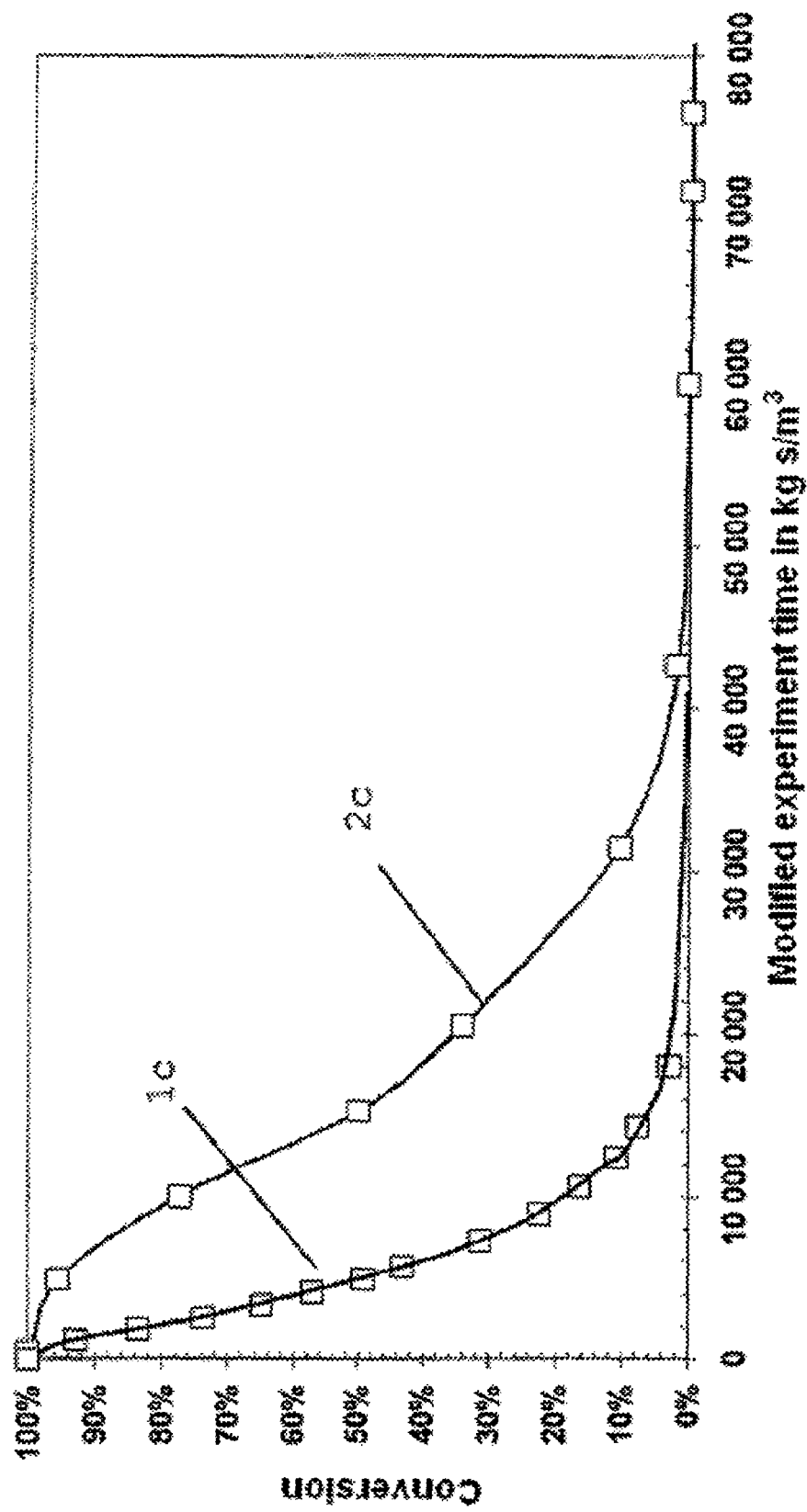
FIG. 3: the relationship between the conversion rate and the modified experiment time of the catalyst without IL-coating (curve 1c) and of the catalyst according to the invention (curve 2c) in the reaction of cyclooctadiene with hydrogen.

In FIG. 3 there are represented the conversion rates for the hydrogenation of cyclooctadiene for the uncharged nickel catalyst (curve 1c) and the nickel catalyst coated with the ionic liquid (curve 2c) in relation to the modified experiment time.

The curves show that the necessary experiment time for a 50% cyclooctadiene conversion for the nickel catalyst coated with the ionic liquid is approx. 5000 kg S/m$^3$, while for the uncoated nickel catalyst an experiment time of approx. 15000 kg s/m$^3$ is necessary for the same conversion rate. It follows that the reaction rate for the nickel catalyst coated with the ionic liquid is slower by a factor of approximately 3.

After the reaction, the nickel catalyst charged with the ionic liquid was dried under vacuum at a temperature of 110° C. and its pore system then characterized by means of BET and Hg porosimetry measurements. The relationship between the pore volumes and the pore diameter and the relationship between the inner surface and the pore diameter is represented by curves 3a and 3b of FIGS. 1 and 2 respectively. The reduction in the pore volume and the inner surface of the coated nickel catalyst respectively is presumably de to the fact that the pores are covered with residues of the solvent dodecane, which has a boiling point of 216° C.

EXAMPLE 5

In order to determine the selectivity of the uncoated nickel catalyst with regard to the hydrogenation reaction, the uncharged nickel catalyst was used during the reaction of cyclooctadiene with hydrogen. The cyclooctadiene was hydrogenated under the following reaction conditions:
$m_{cat}$=0.11 g
$d_{cat}$=125-250 micrometers
$m^0_{cyclooctadiene}$=0.18 g
$V_{dodecane}$=150 ml
T=50° C.
$p_{H2}$=50 bar
n=2000 l/min
$c^0_{cyclooctadiene}$=10.9 mol/m$^3$
$c^0_{H2}$=194 mol/m$^3$.

Figure 4:
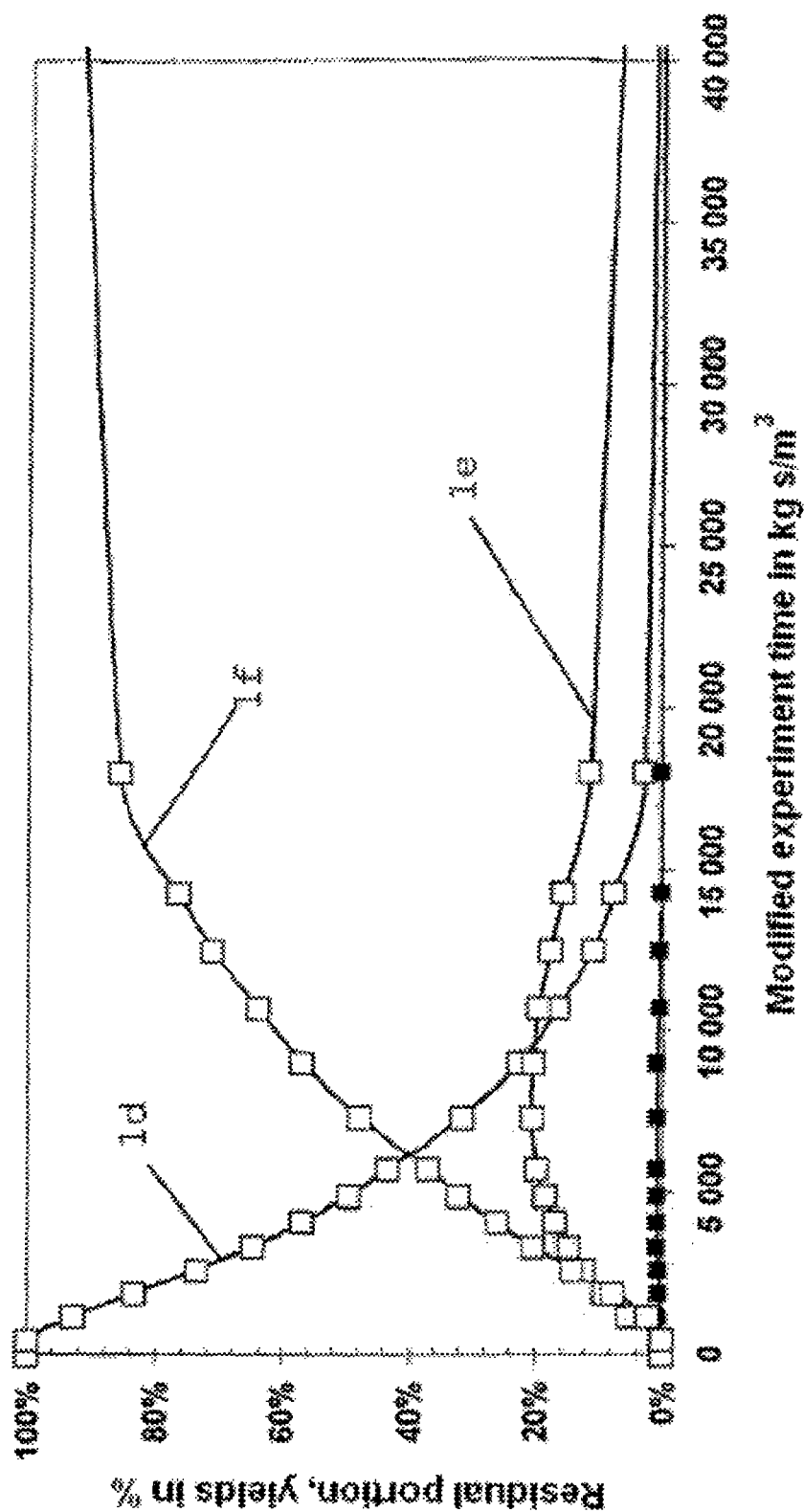
FIG. 4: the residual portion of cyclooctadiene (curve 1d) and cis-cyclooctene (curve 1e) and cyclooctene yield (curve 1f) in relation to the modified experiment time during the hydrogenation of cyclooctadiene by means of the supported nickel catalyst without IL-coating.

In FIG. 4 the development of the residual portion of cyclooctadiene and of the yields of cis-cyclooctene and cyclooctane are represented by the curves numbered 1d, 1e and 1f respectively. 1e shows that the proportion of cis-cyclooctene during the hydrogenation reaction reaches a maximum of approx. 20%, which corresponds to a selectivity with regard to cis-cyclooctene of 26%.

Figure 5:
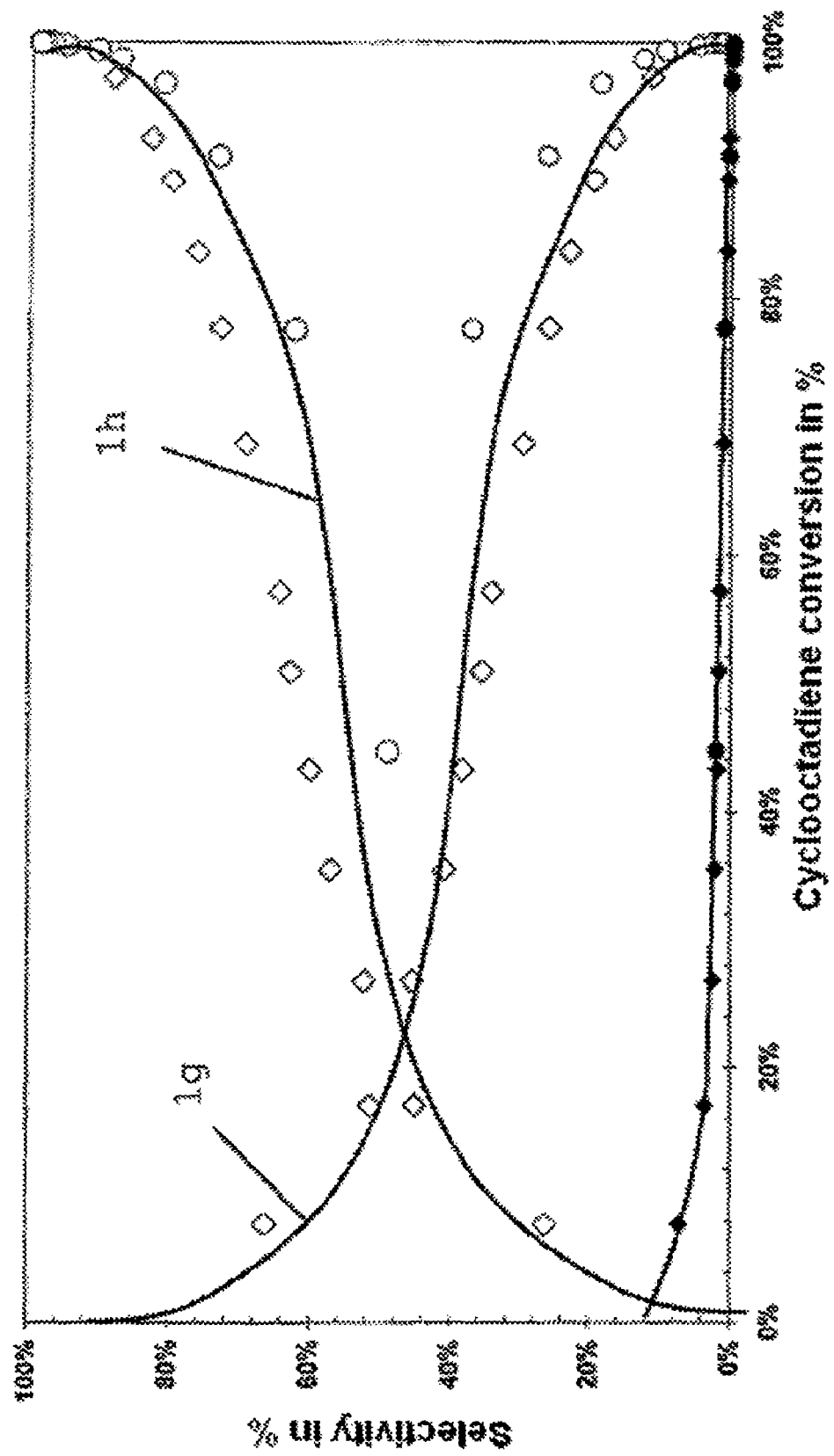
FIG. 5: selectivity with regard to cis-cyclooctene (curve 1g) and cyclooctane (curve 1h) in relation to the cylcooctadiene conversion during the hydrogenation of cyclooctadiene by means of the supported nickel catalyst without IL-coating.
Figure 6:
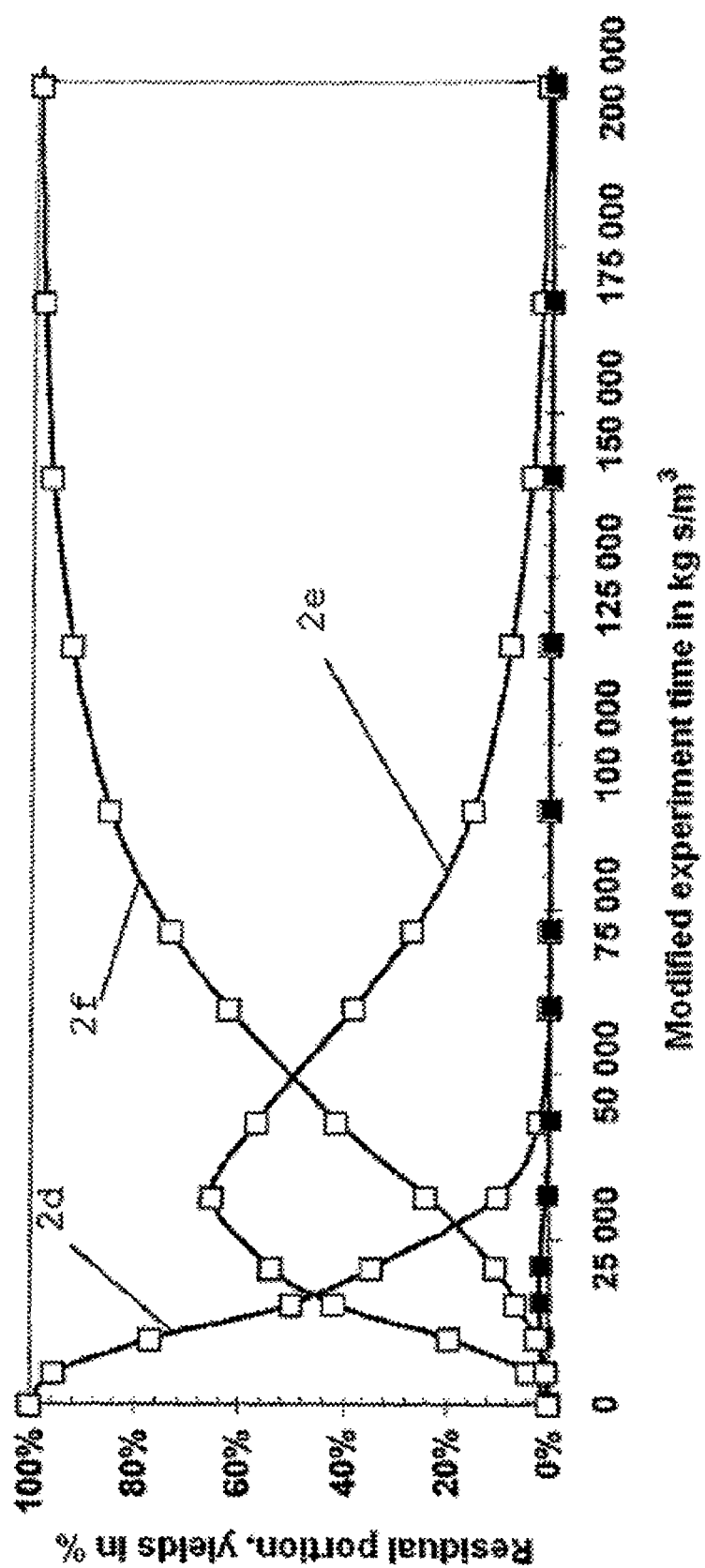
FIG. 6: the residual portion of cyclooctadiene (curve 2d) and cis-cyclooctene (curve 2e) and cyclooctane (curve 2f)

In FIG. 5, the curves 1g and 1h represent the development of the selectivities with regard to the cis-cyclooctene and cyclooctane respectively of the reaction in question. Curve 1g shows a relatively rapid drop in cis-cyclooctene selectivity as cyclooctadiene conversion increases.

EXAMPLE 6

In order to ascertain the selectivity of the nickel catalyst coated with the ionic liquid with regard to hydrogenation reactions, the coated nickel catalyst was used in the hydrogenation of cyclooctadiene under the following reaction conditions:
$m_{cat}$=0.81 g
$d_{cat}$=125-250 micrometers
$m^0_{cyclooctadiene}$=0.17 g
$V_{dodecane}$=150 ml
T=50° C.
$p_{H2}$=50 bar
n=2000 l/min.

The development of the proportions of cyclooctadiene, of cis-cyclooctene and of cyclooctane over the named hydrogenation reaction is represented by the curves numbered 2d, 2e and 2f respectively. Curve 2e has a maximum proportion of cis-cyclooctene of 65%, which corresponds to a selectivity with regard to cis-cyclooctene of 72%. The development of the selectivities with regard to cis-cyclooctene and cyclooctane during the reaction in question are represented in FIG. 7 by means of the curves numbered 2g and 2h respectively. Compared with the uncoated nickel catalyst, the nickel catalyst according to the invention coated with the ionic liquid shows a comparatively slow drop in cis-cyclooctene selectivity as cyclooctadiene conversion during the hydrogenation of cyclooctadiene increases.

What is claimed is:

1. A porous heterogeneous catalyst comprising a preformed supported metal catalyst having a metal deposited on a carrier having an inner surface,
    wherein the inner surface of the catalyst is coated with an ionic liquid (IL) having an average thickness which is greater than or equal to the thickness of one ion layer of the IL and which is less than or equal to the thickness of ten ion layers of the IL, and
    wherein the metal is selected from the group consisting of nickel, cobalt, copper, iron, ruthenium, rhodium, iridium, palladium, and platinum.

2. The porous catalyst according to claim 1, characterized in that the catalyst is formed as powder or as a shaped body.

3. The porous catalyst according to claim 1 characterized in that the BET surface area of the catalyst without the IL-coating is 10 to 300 m$^2$/g.

4. The porous catalyst according to claim 1, characterized in that the integral pore volume of the catalyst without the IL-coating is greater than 100 mm$^3$/g.

5. The porous catalyst according to claim 1, characterized in that the cation of the ionic liquid is selected from compounds of Formulae IL-1 to IL-23:

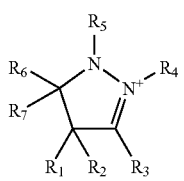 (IL-5)
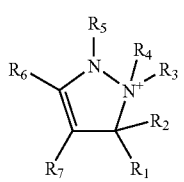 (IL-6)
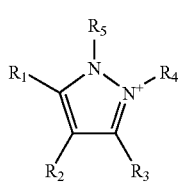 (IL-7)
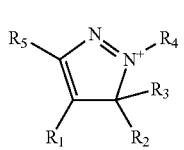 (IL-8)
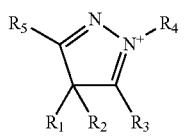 (IL-9)
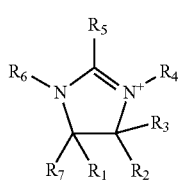 (IL-10)
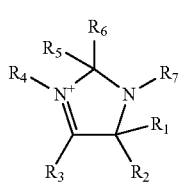 (IL-11)
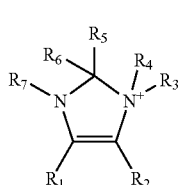 (IL-12)
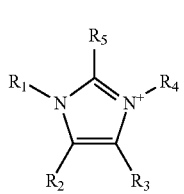 (IL-13)
(IL-14)
(IL-15)
(IL-16)
(IL-17)
(IL-18)
(IL-19)
(IL-20)
(IL-21)
(IL-22)

-continued

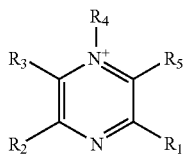
(IL-23)

wherein the radicals $R_1, R_2, R_3, R_4, R_5, R_6, R_7, R_8, R_9$ and $R_{10}$ each independently of one another are hydrogen, or a functional group, wherein two of the functional groups can be linked together with formation of an unsaturated or saturated ring segment which can optionally be interrupted by one or more oxygen and/or sulphur atoms and/or one or more substituted or unsubstituted imino groups, wherein the ring segment can be substituted by functional groups, and wherein $R_4$ in addition can be selected from the group of radicals consisting of $C_1$-$C_{18}$ alkyloyl, $C_1$-$C_{18}$ alkyloxycarbonyl, $C_5$-$C_{12}$ cycloalkylcarbonyl and $C_6$-$C_{12}$ aryloyl, wherein each is optionally substituted by one or more functional groups.

6. The porous catalyst according to claim 5 wherein the functional groups $R_1$-$R_{10}$ are radicals selected from the group consisting of aryl, alkyl, arloxy, alkyloxy, halogen, heteroatom and/or heterocycle-substituted $C_1$-$C_{18}$ alkyl, and a five- to six-membered heterocycle having oxygen, nitrogen and/or sulphur atoms, wherein two of the named radicals can be linked together with formation of an unsaturated or saturated ring segment which can optionally be interrupted by one or more oxygen and/or sulphur atoms and/or one or more substituted or unsubstituted imino groups, wherein the ring segment can be substituted by functional groups, aryl, alkyl, aryloxy, alkyloxy, halogen, heteroatom and/or heterocycle radicals, and wherein $R_4$ in addition can be selected from the group of radicals consisting of $C_1$-$C_{18}$ alkyloyl, $C_1$-$C_{18}$ alkyloxycarbonyl, $C_5$-$C_{12}$ cycloalkylcarbonyl and $C_6$-$C_{12}$ aryloyl, wherein the members of the named group can each be substituted by one or more, aryl, alkyl, aryloxy, alkyloxy, halogen, heteroatoms and/or heterocycle radicals, wherein $C_1$-$C_{18}$, refers to the alkyl chain, $C_5$-$C_{12}$ refers to cycloalkyl group and/or $C_6$-$C_{12}$ refers to the aryl group.

7. The porous catalyst according to claim 1, characterized in that the anion of the ionic fluid is selected from the group consisting of $F^-$, $Cl^-$, $Br^-$, $I^-$, $PF_6^-$, $BF_4^-$, alkyl sulphate, ether sulphate, acetate, trifluoroacetate, triflate, sulphate, hydrogensulphite, methyl sulphate, ethyl sulphate, sulphite, hydrogensulphite, aluminium chlorides, aluminium tribromide, nitrite, nitrate, metal complexes, phosphates, phosphate, hydrogen phosphate, dihydrogen phosphate, carbonate, hydrogen carbonate, sulphonate, tosylate, bis(trifluoromethylsulphonyl)imide, cyanide and isocyanate.

8. The porous catalyst according to claim 1, characterized in that the IL-coating contains a homogeneous catalyst.

9. The porous catalyst according to claim 1, wherein the catalyst support is produced using a material selected from the group consisting of titanium oxide, silicon oxide, aluminium oxide, zirconium oxide, magnesium oxide, silicon carbide, magnesium silicate, zinc oxide, zeolites and nanomaterials.

\* \* \* \* \*

UNITED STATES PATENT AND TRADEMARK OFFICE
CERTIFICATE OF CORRECTION

PATENT NO. : 8,334,232 B2
APPLICATION NO. : 12/298246
DATED : December 18, 2012
INVENTOR(S) : Jess et al.

It is certified that error appears in the above-identified patent and that said Letters Patent is hereby corrected as shown below:

In column 18, (IL 4), line 65 (Approx.), in Claim 5, delete "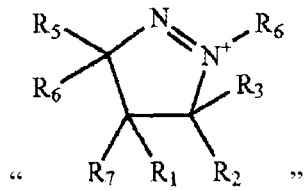"

and insert

-- 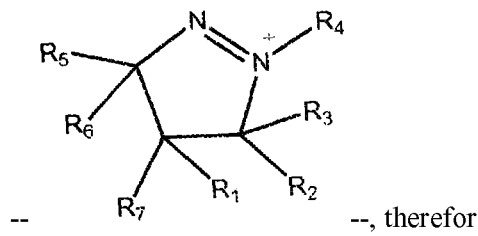 --, therefor

Signed and Sealed this
Second Day of April, 2013

Teresa Stanek Rea
*Acting Director of the United States Patent and Trademark Office*